United States Patent
Omoto et al.

(10) Patent No.: US 10,829,447 B2
(45) Date of Patent: Nov. 10, 2020

(54) METHIONINE PRODUCTION METHOD AND PRODUCTION EQUIPMENT

(71) Applicant: SUMITOMO CHEMICAL COMPANY, LIMITED, Tokyo (JP)

(72) Inventors: Norihito Omoto, Niihama (JP); Yoshitaka Satoh, Niihama (JP); Masayuki Morikawa, Niihama (JP); Yoshiyuki Koizumi, Niihama (JP); Naoya Yamashiro, Niihama (JP); Ryousuke Katagami, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/608,038

(22) PCT Filed: Apr. 27, 2018

(86) PCT No.: PCT/JP2018/017210
§ 371 (c)(1),
(2) Date: Dec. 3, 2019

(87) PCT Pub. No.: WO2018/199294
PCT Pub. Date: Nov. 1, 2018

(65) Prior Publication Data
US 2020/0079730 A1 Mar. 12, 2020

(30) Foreign Application Priority Data

Apr. 27, 2017 (JP) .................................. 2017-087751

(51) Int. Cl.
*C07C 319/20* (2006.01)
*C07C 319/28* (2006.01)
*C07C 323/58* (2006.01)
*B01J 19/00* (2006.01)

(52) U.S. Cl.
CPC ......... *C07C 319/20* (2013.01); *B01J 19/0046* (2013.01); *C07C 319/28* (2013.01); *B01J 2219/00033* (2013.01); *C07C 323/58* (2013.01)

(58) Field of Classification Search
CPC .. C07C 319/20; C07C 323/58; B01J 19/0046; B01J 2219/00033
See application file for complete search history.

(56) References Cited

U.S. PATENT DOCUMENTS

| 2,867,503 A * | 1/1959 | Roy .................... C22B 23/0461 |
| | | 423/141 |
| 7,655,072 B2 * | 2/2010 | Hasselbach ............ B01D 53/62 |
| | | 423/242.2 |
| 2007/0055078 A1 | 3/2007 | Shiozaki et al. |
| 2010/0121103 A1 | 5/2010 | Koizumi et al. |
| 2015/0038739 A1 | 2/2015 | Nishida et al. |
| 2015/0051421 A1 | 2/2015 | Koerfer et al. |

FOREIGN PATENT DOCUMENTS

| GB | 2 138 792 A | 10/1984 |
| JP | 60-108357 A | 6/1985 |
| JP | 2007-63141 A | 3/2007 |
| JP | 2010-111641 A | 5/2010 |
| JP | 2013-173717 A | 9/2013 |
| JP | 2015-515458 A | 5/2015 |
| JP | 2015-140342 A | 8/2015 |

OTHER PUBLICATIONS

International Preliminary Report on Patentability and the Written Opinion of the International Searching Authority for International Application No. PCT/JP2018/017210, dated Oct. 29, 2019.
International Search Report for International Application No. PCT/JP2018/017210 dated Jul. 31, 2018.

* cited by examiner

*Primary Examiner* — Paul A Zucker
(74) *Attorney, Agent, or Firm* — Birch, Stewart, Kolasch & Birch, LLP

(57) ABSTRACT

The present invention provides a method for producing methionine characterized by comprising a step of hydrolyzing 5-[2-(methylthio)ethyl]imidazolidine-2,4-dione in the presence of an alkali compound to obtain a reaction solution containing an alkali salt of methionine, a step of precipitating methionine by introducing carbon dioxide into the reaction solution to obtain a first slurry containing the methionine, a step of allowing the first slurry to flow into a pressurized filter and obtaining the solid methionine and mother liquor from the first slurry, and a step of recovering carbon dioxide from the mother liquor. By the present production method, the carbon dioxide introduced in the crystallization step is suppressed from being released from the mother liquor, and the carbon dioxide can be recovered.

4 Claims, 1 Drawing Sheet

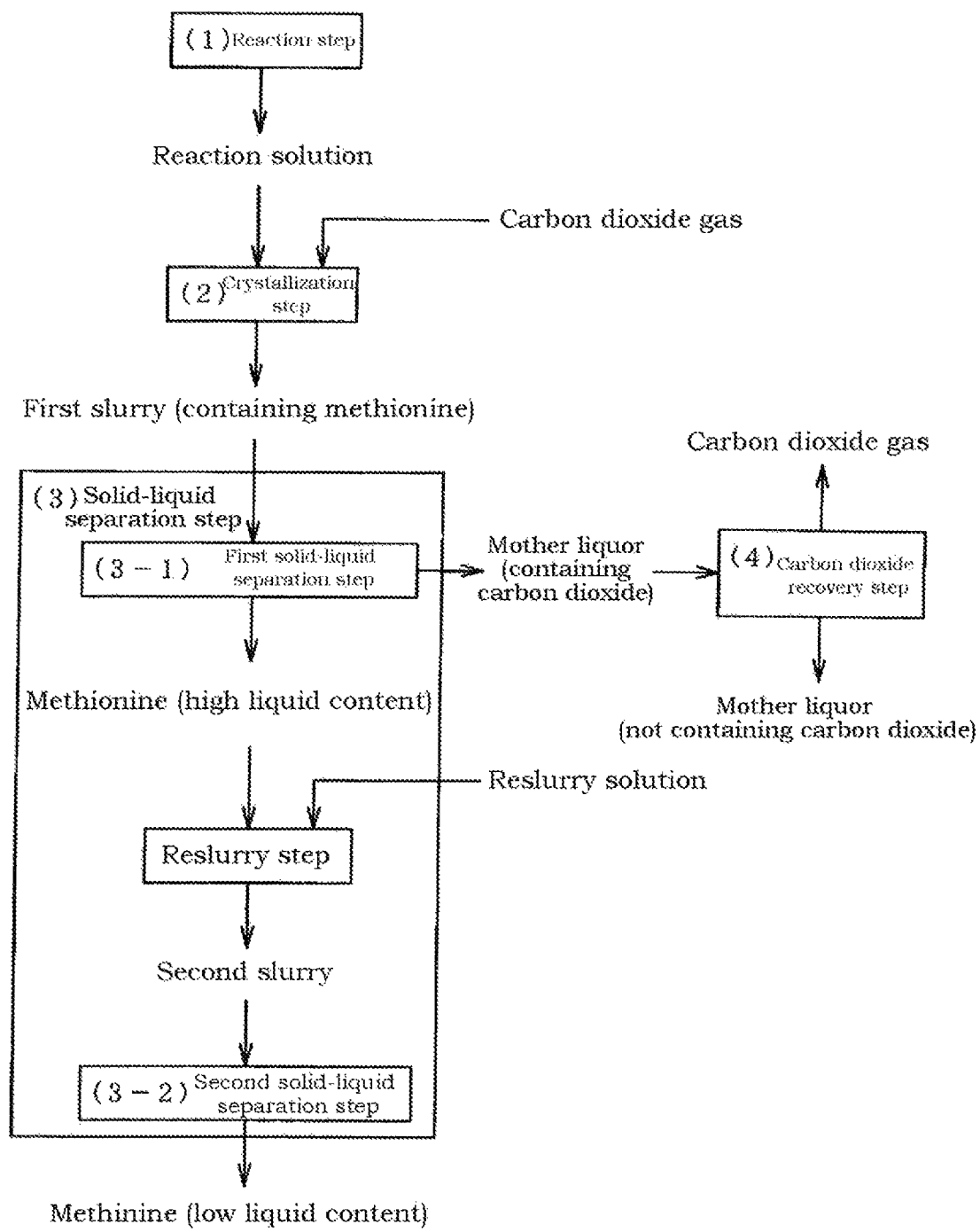

METHIONINE PRODUCTION METHOD AND PRODUCTION EQUIPMENT

TECHNICAL FIELD

This application claims priority to and the benefit of Japanese Patent Application No. 2017-087751 filed Apr. 27, 2017, the entire contents of which are incorporated herein by reference.

The present invention is related to a method for producing methionine by hydrolysis of 5-[2-(methylthio)ethyl]imidazoline-2,4-dione.

BACKGROUND ART

Methionine is one kind of an essential amino acid that cannot be synthesized in a body in an animal, and is widely used as a feed additive for animal, and also is industrially produced by a chemical plant.

As an example of production method of methionine, a method which comprises a crystallizing step in which 5-[2-(methylthio)ethyl]imidazoline-2,4-dione is hydrolyzed, and carbon dioxide gas is then introduced into the resulting reaction solutions to precipitate out methionine is disclosed (for example, see Patent document 1).

CITATION LIST

Patent Document

Patent Document 1: JP 2010-111641 A

SUMMARY OF THE INVENTION

Problems to be Solved By Invention

In the above-mentioned method, after a precipitation of methionine, solid-liquid separation such as filtration and decantation is conducted to separate methionine and mother liquor. Carbon dioxide introduced in the crystallization step is dissolved in the mother liquor, and the carbon dioxide is released as a gas during the solid-liquid separation. If the carbon dioxide can be recovered and recycled, it is possible to reduce the cost in the methionine production and also to reduce the environmental burden due to the release of carbon dioxide into the atmosphere.

In view of the above circumstances, an object of the present invention is to provide a method for producing methionine that is capable of recovering carbon dioxide from mother liquor separated by a solid-liquid separation after the crystallization step and recycling it.

Means to Solve Problems

The present inventors have intensively studied, and as a result, have found that carbon dioxide can be recovered from the separated mother liquor by conducting a solid-liquid separation after the crystallization step using a pressurized filter.

The present invention encompasses the following embodiments.

[1] A method for producing methionine comprising the following steps (1) to (4):

(1) a reaction step: a step of hydrolyzing 5-[2-(methylthio)ethyl]imidazolidine-2,4-dione in the presence of an alkali compound to obtain a reaction solution containing an alkali salt of methionine, (2) a crystallization step: a step of precipitating methionine by introducing carbon dioxide into the reaction solution to obtain a first slurry containing the methionine, (3) a solid-liquid separation step: a step of allowing the first slurry to flow into a pressurized filter and obtaining the solid methionine and mother liquor from the first slurry, and (4) a carbon dioxide recovery step: a step of recovering carbon dioxide from the mother liquor (hereinafter, referred to as "Method for producing methionine of the present invention").

[2] The method for producing methionine according to the embodiment 1, wherein the solid-liquid separation step comprises a first solid-liquid separation step and a second solid-liquid separation step, and the first solid-liquid separation step is a step of allowing the first slurry to flow into a pressurized filter and obtaining the solid methionine and the mother liquor from the first slurry, and the second solid-liquid separation step is a step of further reducing the liquid content of solid methionine (for example, cake or powder thereof) obtained in the first solid-liquid separation step by drying or filter pressing.

[3] The method for producing methionine according to the embodiment 2, which comprises a reslurry step of mixing the solid methionine obtained in the first solid-liquid separation step (for example, a cake or powder thereof) and a reslurry solution (that is, a solution for reslurry) to form a second slurry, and the second solid-liquid separation step comprises a step of conducting a solid-liquid separation of the second slurry to obtain solid methionine having lower liquid content than the solid methionine obtained in the first solid-liquid separation step.

[4] The method for producing methionine according to any one of the embodiments 1 to 3, wherein the said pressurized filter is a continuous pressurized filter.

[5] A production apparatus comprising a reaction apparatus for hydrolyzing 5-[2-(methylthio)ethyl]imidazolidine-2,4-dione in the presence of an alkali compound to obtain a reaction solution containing an alkali salt of methionine, a crystallization apparatus for precipitating methionine by introducing carbon dioxide into the reaction solution to obtain a first slurry containing the methionine, a pressurized filtration apparatus for obtaining the solid methionine and the mother liquor from the first slurry, and a carbon dioxide recovery apparatus for recovering carbon dioxide from the mother liquor, (hereinafter, referred to as "Production apparatus of methionine of the present invention").

[6] The production apparatus of methionine according to embodiment 5 wherein a solid-liquid separation apparatus is provided in downstream of the pressurized filtration facility.

[7] The production apparatus of methionine according to embodiment 5 or 6, wherein the pressurized filtration apparatus is a continuous pressurized filtration apparatus.

[8] The method for producing methionine according to the embodiment 1, which comprises further a step of drying the methionine obtained in the (5) solid-liquid separation step.

According to the method and apparatus of the present application, the carbon dioxide introduced in the crystallization step is suppressed from being released from the mother liquor by conducting solid-liquid separation after the crystallization step with a pressurized filter to recover carbon dioxide. Recycling the recovered carbon dioxide can reduce the cost at producing methionine and also reduce an environmental burden.

BRIEF DESCRIPTION OF DRAWINGS

The FIGURE indicates a flowchart showing an example of the method for producing methionine which concerns on an embodiment of the method of this application.

MODE FOR CARRYING OUT THE INVENTION

Hereinafter, the present invention is explained based on embodiments of the method and apparatus of the present application. However, the embodiments described below exemplifies a production method of methionine and a production apparatus of methionine for embodying the technical idea of the present invention, and the present invention is not limited to the followings.

As used herein, 5-[2-(methylthio)ethyl]imidazolidine-2,4-dione is used as a raw material, and is hydrolyzed in the presence of an alkali compound to obtain a reaction solution containing methionine as an alkali salt (hereinafter sometimes referred to as "Present reaction solution") [(1) reaction step]. Examples of a method for preparing 5-[2-(methylthio)ethyl]imidazolidine-2,4-dione as a raw material include a method in which 2-hydroxy-4-methylthiobutanenitrile is reacted with ammonia and carbon dioxide or with ammonium carbonate.

Examples of the alkali compound include potassium hydroxide, sodium hydroxide, potassium carbonate, potassium hydrogen carbonate and the like, and two or more of them can be used if necessary.

The amount of the alkali compound used is usually 2 to 10 moles, preferably 3 to 6 moles as potassium or sodium per mole of 5-[2-(methylthio)ethyl]imidazolidine-2,4-dione. The amount of water used is usually 2 to 20 parts by weight per 1 part by weight of 5-[2-(methylthio)ethyl]imidazolidine-2,4-dione.

The hydrolysis reaction conducted in the reaction step is a stirring type or non-stirring type, and is conducted in a continuous type or batch type reaction tank.

This hydrolysis reaction is preferably carried out by heating to about 150 to 200° C. under a pressure of about 0.5 to 1 MPa as a gauge pressure. The reaction period is usually 10 minutes to 24 hours.

In order to obtain methionine from the present reaction solution, a crystallization step is conducted. In the crystallization step, the present reaction solution is allowed to flow into the crystallization apparatus, and carbon dioxide is introduced into the present reaction solution to precipitate methionine, thereby to obtain a first slurry containing the methionine [(2) crystallization step].

Carbon dioxide is absorbed into the reaction solution by introducing carbon dioxide, and thereby an alkali salt of methionine is precipitated as a free methionine. The introduction of carbon dioxide in the crystallization step is preferably carried out under a pressure of 0.1 to 1.0 MPa, preferably 0.2 to 0.5 MPa as a gauge pressure. The crystallization temperature is usually 0 to 50° C., preferably 10 to 30° C. The crystallization time may be indicated by a time until the present reaction solution is saturated with carbon dioxide and methionine is sufficiently precipitated, and is usually 10 minutes to 24 hours.

The first slurry containing the precipitated methionine is subjected to a solid-liquid separation method. In the solid-liquid separation step, an operation is conducted in which the first slurry obtained in the crystallization step is allowed to flow into a pressurized filter, and solid methionine (for example, cake or powder thereof) and mother liquor are obtained from the first slurry. [(3) Solid-liquid separation step]. In the mother liquor, carbon dioxide introduced under pressurized pressure in the above crystallization step is dissolved. In the solid-liquid separation step, solid-liquid separation is conducted using a pressurized filter so that the carbon dioxide is not released as a gas. As the pressurized filter, a filter capable of filtering the slurry in a sealed state is used. Examples of the pressurized filter include a drum pressurized filter, a leaf pressurized filter, a candle pressurized press, a belt press type filter press, a screw press type filter press, and a rotary press type filter press. Also the pressurized filter may be either a continuous type or a batch type, but is preferably a continuous type pressurized filter because productivity is improved.

The pressure in the pressurized filter is 0.1 to 1.0 MPa as a gauge pressure, preferably the same as or higher than the pressure used in the crystallization step. The filtration temperature is usually 0 to 50° C., preferably 10 to 30° C.

The mother liquor obtained in the solid-liquid separation step is transferred to a recovery tank of a carbon dioxide recovery apparatus. Since this recovery tank is kept at a pressure lower than the pressure in the pressurized filter, preferably at atmospheric pressure, the carbon dioxide dissolved in the mother liquor is released as a gas. Since the inside of this recovery tank is sealed, the carbon dioxide that has become a gas is recovered [(4) carbon dioxide recovery step]. The recovered carbon dioxide is recycled to any step in the production of methionine.

The recovery tank of the carbon dioxide recovery apparatus is a so-called flash tank, and the structure thereof is not particularly limited as long as it can separate gas and liquid. In the flash tank of the present embodiment, the mother liquor is introduced from the side of the tank, and the gas and liquid are separated inside the flash tank. The flow rate of the mother liquor to the flash tank is not limited, for example, the size and number of the flash tanks are appropriately determined depending on the solid content concentration in the slurry and the flow rate of the mother liquor.

The FIGURE is a flowchart showing an example of a method for producing methionine according to an embodiment of the production method of the present application. As shown in the FIGURE, the solid-liquid separation step in the present invention may include a first solid-liquid separation step and a second solid-liquid separation step. In this case, the first solid-liquid separation step is a step of allowing the first slurry obtained in the crystallization step to flow into a pressurized filter and obtaining solid methionine and mother liquor from the first slurry, and the second solid-liquid separation step is a step of reducing the liquid content of solid methionine. In the first solid separation step, the purpose is to conduct a solid-liquid separation of the first slurry such that carbon dioxide gas is not released from the mother liquor, and in the second solid-liquid separation step, the purpose is to reduce the liquid content of solid methionine, and each step can be conducted efficiently by using a solid-liquid separator according to the purpose. Also, in order to improve productivity, it is preferable to use a continuous pressurized filter in the first solid-liquid separation step. By conducting the first solid-liquid separation step using a continuous pressurized filter, and then conducting the second solid-liquid separation step, carbon dioxide gas can be recovered from the mother liquor and productivity is improved. The solid-liquid separation in the second solid-liquid separation step is conducted by a filtration and a decantation and the like. In the present invention, the solid-liquid separation in the second solid-liquid separation step is preferably conducted by a centrifugation. In the second solid-liquid separation step, the solid-liquid separation is conducted such that the liquid content of the solid methionine is 1 to 25% by weight.

Here as used herein, the "downstream side" means the side close to the step of obtaining the final product in the method for producing methionine of the present invention.

The present invention may encompass a reslurry step in which the methionine obtained in the first solid-liquid separation step and the reslurry solution are mixed to form a second slurry. The term of "Reslurry" generally refers to an operation in which a solid obtained by a solid-liquid separation of a slurry is mixed with a liquid to form a slurry again, and a liquid in which the solid is difficult to dissolve is used. The term of "reslurry liquid" as used herein means a liquid used for reslurry. As the reslurry liquid, a liquid in which methionine is difficult to dissolve is used, and a saturated aqueous solution of methionine is preferably used.

When the present invention comprises a reslurry step, the liquid content of solid methionine is further reduced by a solid-liquid separation of the second slurry obtained in the reslurry step in the second solid-liquid separation step. The second solid-liquid separation step is conducted by the above method. The amount of impurities contained in the methionine is reduced by reslurrying the solid methionine obtained in the first solid-liquid separation step. Further, the amount of impurities contained in methionine can be further reduced by reducing the liquid content.

As the second solid-liquid separation step, when the reslurry step is not comprised, a method of reducing the water content of the solid methionine obtained in the first solid-liquid separation step as it is considered. Specifically, the liquid in the solid methionine is removed by drying or filter pressing. The pressure at this time does not matter, however, it is often more energy efficient to carry out under reduced pressure. Examples of drying methods include material transport method, material static type, material transfer type, material agitation type, and hot air transfer type, and examples of a heat transfer method for drying include a convection heat transfer method, a conduction heat transfer method, a radiant heat transfer method, and a microwave heating method and the like. Examples of a method of reducing the liquid content include a method by a mechanical pressure such as a filter press such as a belt press type filter press, a screw press type filter press or a rotary press type filter press.

The methionine obtained in the solid-liquid separation method is dried to be a final product. Drying is conducted by heating to about 50 to 120° C. under a slight reduced pressure. The drying period is usually 10 minutes to 24 hours.

EXAMPLES

Next, examples of the present invention are shown, however the present invention is not limited thereto. In the examples below, parts by weight/hr represents a flow rate per hour.

Example 1

Methionine is precipitated by introducing carbon dioxide gas into the present reaction solution under conditions of a gauge pressure of 0.35 MPa and 25° C. to obtain a slurry containing the precipitated methionine. The slurry is allowed to flow into a pressurized filter under conditions of a gauge pressure of 0.35 MPa and 25° C., and methionine and mother liquor are separated by pressurized filtration using a filter. The mother liquor is allowed to flow into the flash tank at a flow rate of 118.3 parts by weight/hr under conditions of a gauge pressure of 0.35 MPa and 25° C. In the mother liquor, 18.3 parts by weight of carbon dioxide is dissolved per 118.3 parts by weight of the mother liquor. Under the condition that the pressure in the flash tank is 0 MPa (atmospheric pressure) and 25° C., carbon dioxide that has become gas is recovered from the flash tank. The amount of carbon dioxide recovered is 14.5 parts by weight/hr in terms of gas flow rate. Also 0.2 parts by weight/hr of water is recovered.

The invention claimed is:

1. A method for producing methionine which comprises the following steps (1) to (4):
   (1) a reaction step: a step of hydrolyzing 5-[2-(methylthio)ethyl]imidazolidine-2,4-dione in the presence of an alkali compound to obtain a reaction solution containing an alkali salt of methionine, wherein the alkali compound is selected from the group consisting of potassium hydroxide, sodium hydroxide, potassium carbonate, potassium hydrogen carbonate, and two or more of them,
   (2) a crystallization step: a step of precipitating methionine by introducing carbon dioxide into the reaction solution to obtain a first slurry containing the methionine,
   (3) a solid-liquid separation step: a step of allowing the first slurry to flow into a pressurized filter and obtaining the solid methionine and mother liquor from the first slurry, and
   (4) a carbon dioxide recovery step: a step of recovering carbon dioxide from the mother liquor, wherein the mother liquor is transferred to a recovery tank kept at a pressure lower than the pressure in the pressurized filter, the carbon dioxide dissolved in the mother liquor is released as a gas in the recovery tank, and recovered.

2. The method for producing methionine according to claim 1, wherein the solid-liquid separation step comprises a first solid-liquid separation step and a second solid-liquid separation step, and the first solid-liquid separation step is a step of allowing the first slurry to flow into a pressurized filter and obtaining the solid methionine and the mother liquor from the first slurry, and the second solid-liquid separation step is a step of further reducing the liquid content of solid methionine obtained in the first solid-liquid separation step by drying or filter pressing.

3. The method for producing methionine according to claim 2, which comprises a reslurry step of mixing the solid methionine obtained in the first solid-liquid separation step and a reslurry solution to form a second slurry, and the second solid-liquid separation step comprises a step of conducting a solid-liquid separation of the second slurry to obtain solid methionine having a lower liquid content than the solid methionine obtained in the first solid-liquid separation step.

4. The method for producing methionine according to claim 1, wherein the said pressurized filter is a continuous pressurized filter.

* * * * *